US00PP10863P

United States Patent [19]

Bull

[11] Patent Number: Plant 10,863

[45] Date of Patent: Apr. 20, 1999

[54] NEW GUINEA IMPATIENTS PLANT NAMED 'CLARAMARIE'

[76] Inventor: Norbert Bull, Gaertnersiedlung 2, 24610 Goennebek, Germany

[21] Appl. No.: 08/880,235

[22] Filed: Jun. 23, 1997

[51] Int. Cl.[6] ..... A01H 5/00

[52] U.S. Cl. ..... Plt./318

[58] Field of Search ..... Plt./87.6, 318

[56] References Cited

U.S. PATENT DOCUMENTS

P.P. 8,410 10/1993 Guillen ..... Plt./87.6
P.P. 9,147 5/1995 Kientzler ..... Plt./87.6

OTHER PUBLICATIONS

GTITM UPOVROM Citation for 'Claramarie' as per NL PBR BLM0124, Mar. 16, 1992.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Claramarie', characterized by its pure white flower color, large round flowers, medium green foliage without variegation, medium plant habit, and early to medium flowering response.

1 Drawing Sheet

The present invention comprises a new and distinct cultivar of New Guinea Impatiens, referred to by the cultivar name 'Claramarie'.

'Claramarie' is a product of a planned breeding program and was originated from a hybridization made by the inventor Norbert Bull in a controlled breeding program in Goennebek, Germany, in 1989. The female parent was a seedling designated no. 51 and the male parent was a seedling designated no. 50. Both parents are proprietary cultivars used in the breeding program.

'Claramarie' was discovered and selected as one flowering plant within the progeny of the stated cross by the inventor in 1989 in a controlled environment in Goennebek, Germany.

The first act of vegetative or asexual reproduction of 'Claramarie' was accomplished when cuttings were taken from the initial selection in 1990 in a controlled environment in Goennebek, by, or under the supervision of, Norbert Bull.

Horticultural examination of plants grown from cuttings of the clone initiated in Spring 1991 in Goennebek, Germany, and continuing thereafter, has demonstrated that the combination of characteristics as herein disclosed for 'Claramarie' are firmly fixed and are retained through successive generations of asexual reproduction.

'Claramarie' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Claramarie' which in combination distinguish this Impatiens as a new and distinct cultivar:

1. Pure white flower color.
2. Large, round flowers.
3. Medium green foliage without variegation.
4. Medium plant habit.
5. Early to medium flower response.

Of the many commercial cultivars known to the present inventor, the most similar in comparison to 'Claramarie' is the cultivar 'Jasius', disclosed in U.S. Plant Pat. No. 7,345. In comparison to 'Jasius', 'Claramarie' has somewhat lighter green foliage, smaller leaves, and a shorter plant habit.

The accompanying photographic drawing shows typical flower and foliage characteristics of 'Claramarie' with colors being as true as possible with illustrations of this type. In this regard, the illustration does not accurately depict the true color of the cultivar's eye zone area as it is described in the botanical description.

In the following description color references are made to The Royal Horticultural Society Colour Chart.

The color values were determined indoors from flowers taken from plants grown in Hillscheid, Federal Republic of Germany, under greenhouse conditions which approximate those generally used in commercial practice. The description is based on plants which were planted as rooted cuttings in 10 cm pots and grown at 20° C. minimum temperature.

Classification:

*Botanical.*—A hybrid of the genus Impatiens.

*Commercial.*—New Guinea Impatients cv. 'Claramarie'.

Plant

A. General apparance and form:

*Habit.*—Moderately compact, uniformly molded, medium vigor, freely self-branching, and growth is indeterminate, although weak after flowering begins.

*Height.*—12 cm.

*Width.*—30 cm.

*Internode length.*—35–40 mm.

*Stem color.*—Light to medium green.

*Flowering response.*—About 7 weeks after planting of rooted cuttings.

*Flowering season.*—Generally indeterminate, mainly from March to October, depending on light intensity.

*Lasting quality of the bloom.*—About three weeks.

*Propagation.*—Usually terminal tips for cuttings.

*Rooting.*—Color is R.H.S. 159 B-C; roots initiate in about 18 days at 22° C., from sticking to transplanting; no distinguishing rooting habit.

B. Foliage:

*Leaf arrangement.*—Primarily in whorls.

*Shape of leaf.*—Narrow ovate to elliptic, with acute base and slightly acuminate apex.

*Margin.*—Slightly serrated, ciliated.

*Leaf, length.*—About 110 mm.

*Leaf, width.*—40–43 mm.

*Main color of upper surface.*—Medium green, approximately R.H.S. 137B.

*Veins on upper surface, color.*—Light green.

*Variegation on leaf.*—Absent.

*Main color of lower surface.*—Light green, about R.H.S. 138B.

*Veins on lower surface, color.*—Greenish white.

*Petiole, color.*—Greenish white.

*Petiole, length.*—About 10 mm.

Inflorescence

A. Flower:

*Flower number per node.*—About 6–9, in various stages of development, usually one flower per leaf.

*Form of corolla.*—Single.

*Shape.*—Nearly round, flat with petals overlapping.

*Average diameter.*—60–63 mm.

*Color (general tonality from a distance of three meters).*—White about R.H.S. 155D.

*Petal number.*—Five (5).

*Petal shape.*—Heart-shaped, weakly lobed.

*Petal size.*—The four (4) lower petals are about 30 mm in width and the upper petal is about 35 mm in width; the petal length is about 30 mm.

*Petal texture.*—Smooth, slightly glossy.

*Main color of upper surface.*—R.H.S. 155D.

*Color of lower surface.*—Mainly R.H.S. 155D.

*Color of eye zone.*—R.H.S. 4D and center surrounding ovary is about R.H.S. 150 C-D.

*Spur, color.*—145 D greenish white.

*Spur shape and size.*—Downwardly curved, about 45–50 mm in length.

*Pedicel, color.*—145 C light green.

Reproductive Organs

Androecium:

*Stamens.*—Five (5) in number, fused, upper surface color is about R.H.S. 155 A to R.H.S. 150 D.

*Anthers.*—Hooded, about R.H.S. 11 D.

*Pollen.*—Color is about R.H.S. 4 D.

Gynoecium:

*Stigma and style.*—Five (5) in number, very short, nearly colorless, about R.H.S. 11 D.

*Ovary.*—Five (5) celled, 5 mm in length, surface color is R.H.S. 137 B.

I claim:

1. A new and distinct cultivar of New Guinea Impatiens plant named 'Claramarie', as illustrated and described.

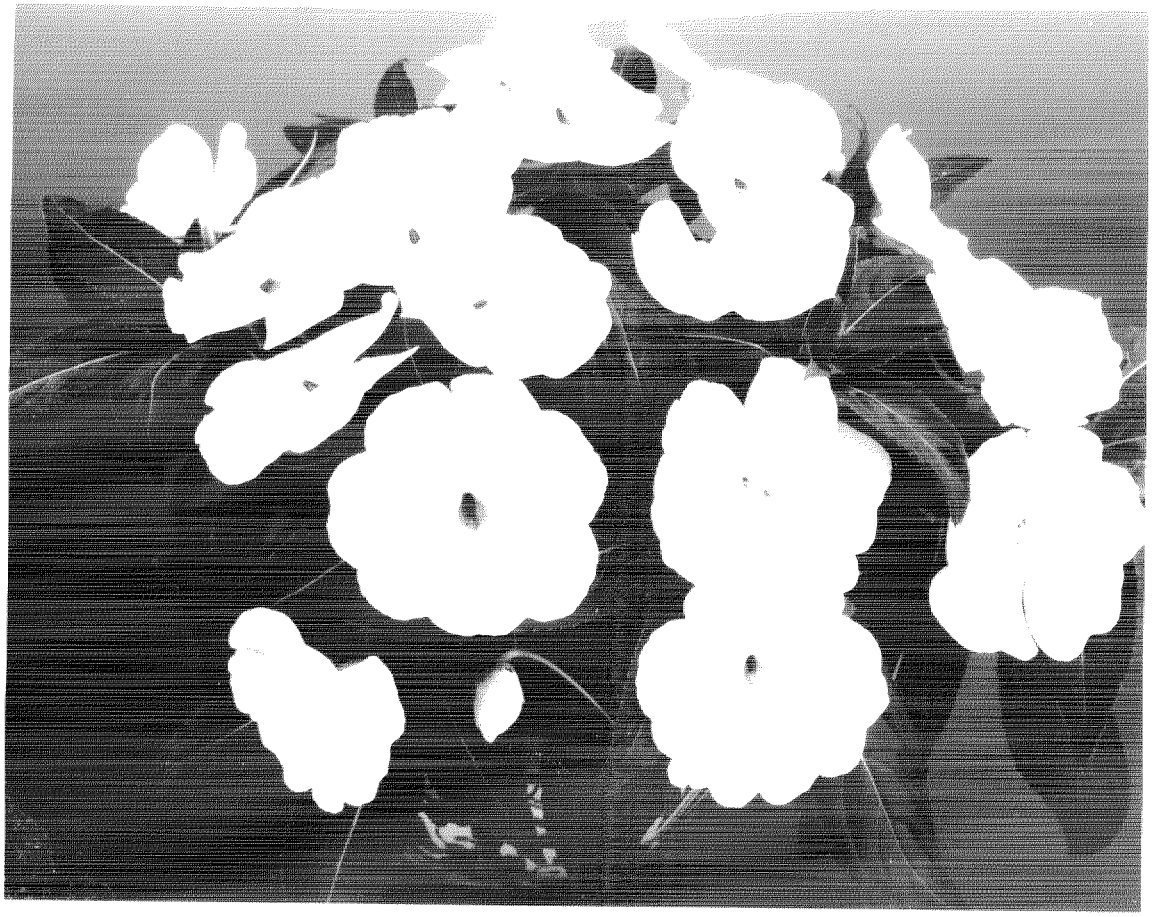

* * * * *